United States Patent

Gubich

Patent Number: 5,242,453
Date of Patent: Sep. 7, 1993

[54] DEVICE FOR PUCKERING THE FLESH TO FACILITATE INJECTIONS

[76] Inventor: Stephen J. Gubich, 3042 Middletown Rd., Bethlehem, Pa. 18017

[21] Appl. No.: 945,187

[22] Filed: Sep. 15, 1992

Related U.S. Application Data

[63] Continuation-in-part of Ser. No. 723,606, Jul. 1, 1991, Pat. No. 5,147,306.

[51] Int. Cl.$^5$ .................................................. A61M 5/00
[52] U.S. Cl. .................................... 604/115; 24/567
[58] Field of Search .................. 604/115, 116, 250; 606/205, 206, 207, 208, 209, 210, 157, 158; 24/509, 510, 567

[56] References Cited

U.S. PATENT DOCUMENTS

| | | | |
|---|---|---|---|
| 2,043,555 | 6/1936 | Preston | 24/509 X |
| 2,493,305 | 1/1950 | McKinney | 24/509 |
| 3,357,126 | 12/1967 | Klieves | 24/567 X |
| 4,968,078 | 11/1990 | Fitzwater | 24/509 X |
| 5,147,306 | 9/1992 | Gubich | 604/115 |

Primary Examiner—Gene Mancene
Assistant Examiner—Thomas Price
Attorney, Agent, or Firm—O'Keefe & Wilkinson

[57] ABSTRACT

A self-injection facilitating device is made in the form of two arm portions having body contacting jaws at one end and manipulating handles at the other. The jaws are biased toward each other by a spring and have a sharp taper at the inner sides opposed to each other to effectively grasp the flesh at the surface of the body when applied thereto in order to pucker the flesh into a small mound into which an injection can conveniently be made with a hypodermic needle using only one hand. An adjustment arrangement for either the position of the pivot point of the arm portions or the distance of the arms apart at the pivot point is provided.

16 Claims, 5 Drawing Sheets

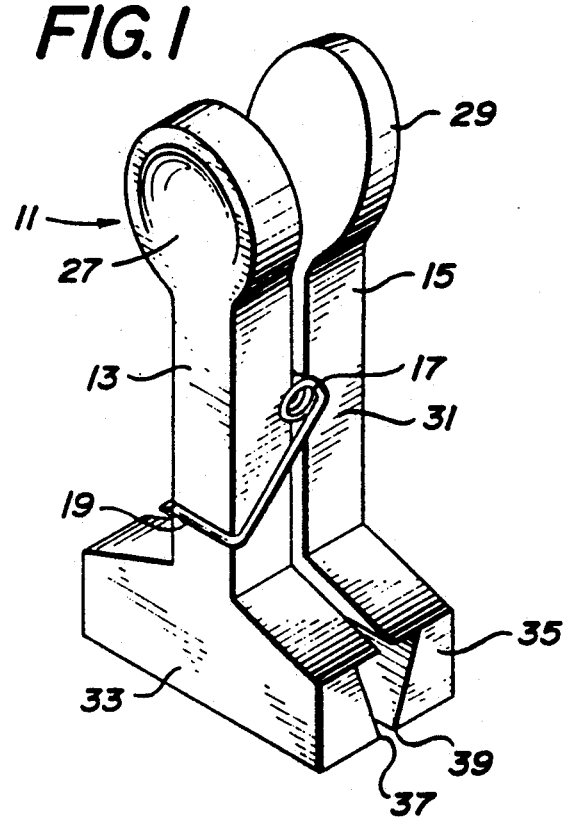
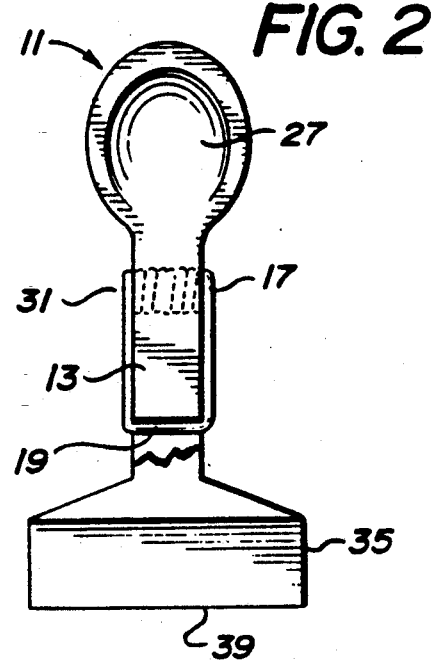
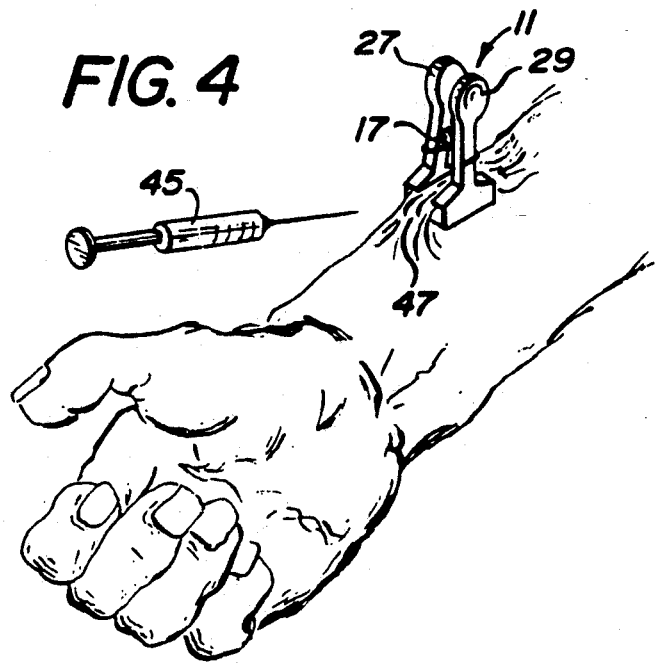
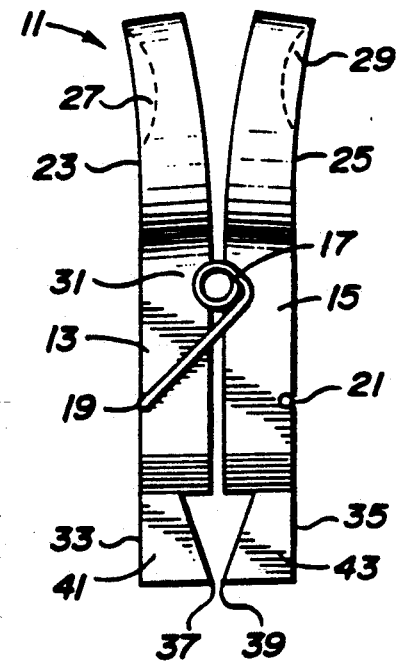

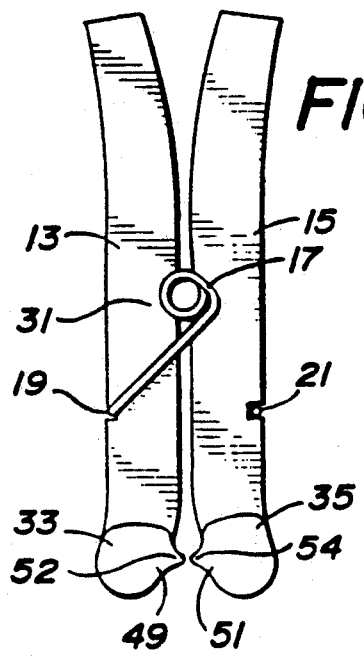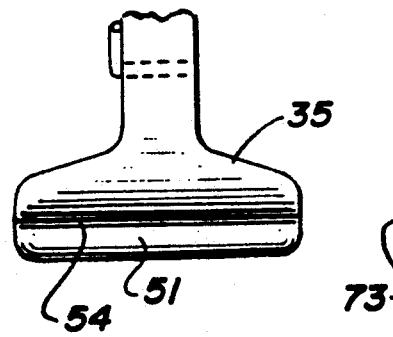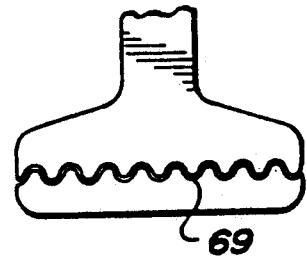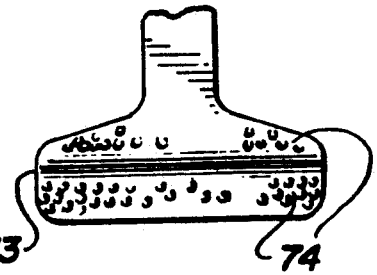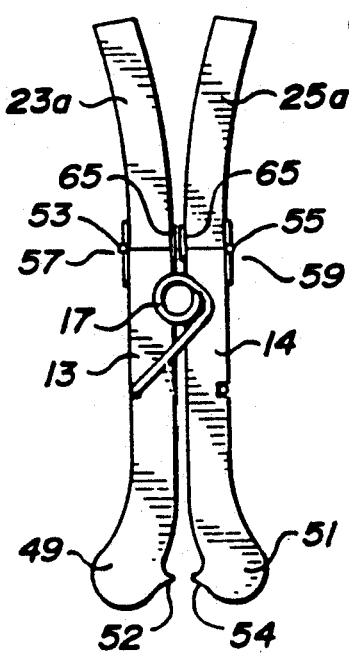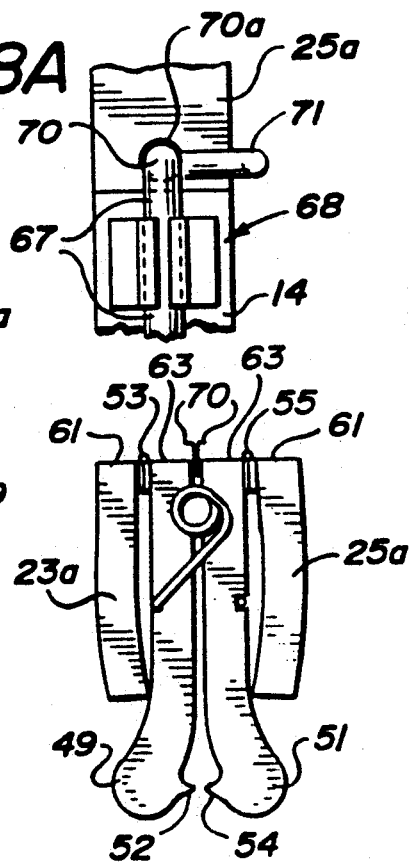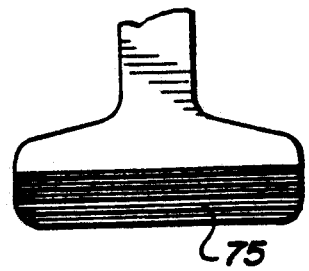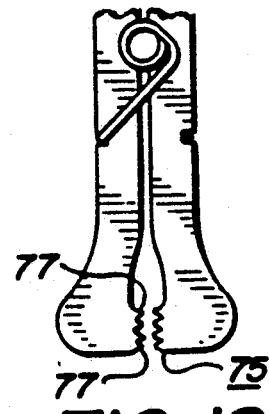

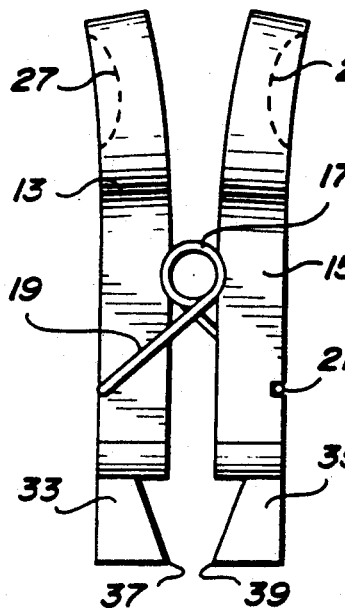
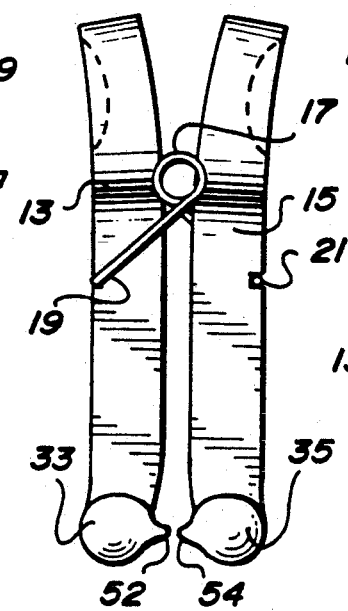
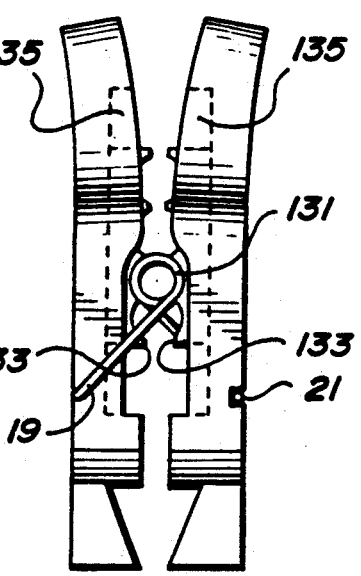
FIG. 23  FIG. 24  FIG. 25
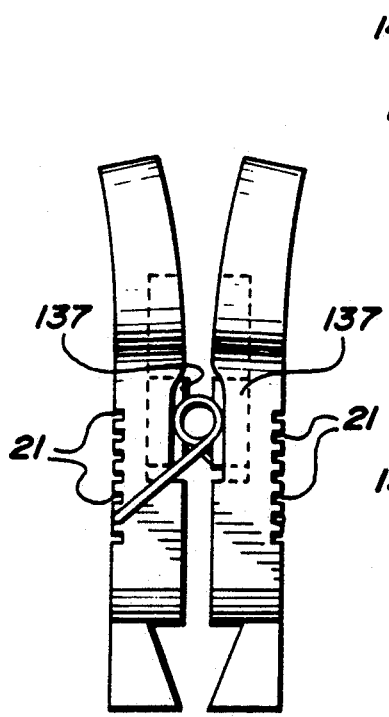
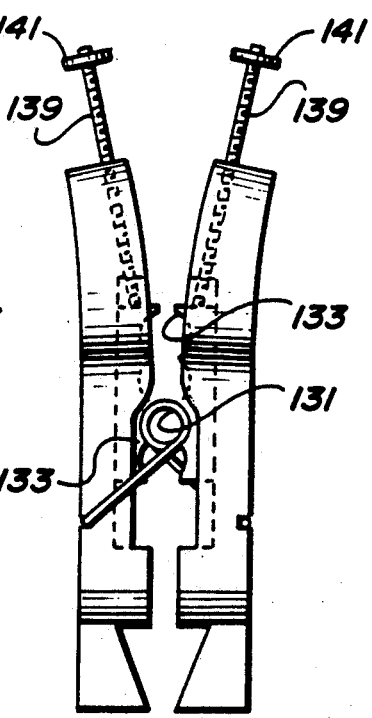
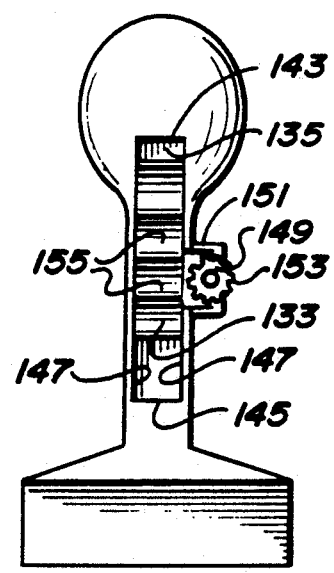
FIG. 26  FIG. 27  FIG. 28
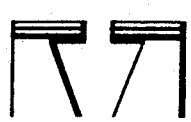

DEVICE FOR PUCKERING THE FLESH TO FACILITATE INJECTIONS

REFERENCE TO PRIOR APPLICATION

This application is a continuation-in-part of my prior application Ser. No. 07/723,606 filed Jul. 1, 1991, now U.S. Pat. No. 5,147,306.

BACKGROUND OF THE INVENTION (1) Field of the Invention

This invention relates broadly to providing medicinal injections into the human body and particularly medicinal injections self-administered by the patient such as insulin injections. More particularly, the invention relates to devices for retracting or puckering the flesh at the surface of the body in order to provide subcutaneous injections of medicinal materials.

(2) Description of the Prior Art

Injections into the human body may be broadly classified into three separate categories:

(A) Intravenous injections which are provided directly into the blood stream or into a blood vessel. Intravenous injections are often given with the same or similar apparatus as is used for drawing blood from the human body for medical analysis purposes.

(B) Subcutaneous injections are provided into the tissue just under the skin. Subcutaneous injections are given when it is desired to apply a medicinal substance to the body without having it immediately disbursed in the blood to other parts of the body. Subcutaneous injections usually provide a slower release of a medicinal substance into the body and thus guard against over-reaction in other portions of the body. Intramuscular injections may be occasionally characterized as subcutaneous injections, although the typical subcutaneous injection is into the fascia and fat tissue just under the skin.

(C) Deep tissue injections are made to internal organs such as, for example, to the heart muscle or other muscles of the body or to other non-muscular organs. Deep tissue injection is rather closely related to needle-type biopsy and it is consequently often applied with similar devices and apparatus except for the size of the needle or trocar.

Deep tissue injections usually are given directly without the aid of any external apparatus other than a long needle or trocar. Occasionally an indexing device for positioning the needle or trocar with respect to external portions of the body in order to more effectively direct an injection into specific internal organs is used.

Intravenous injections are often administered without the use of any external apparatus other than the skilled hands of a hospital or other health care professional and the necessary hypodermic needle. However, devices have also been developed for aiding in the administration of such injections. Most such devices have been designed to aid in isolating a suitable vein near the surface of the body in order to facilitate the injection. While the best device for locating suitable veins is still the sight and feel of a skilled technician, mechanical devices can sometimes aid in such endeavors, particularly when used by less experienced personnel.

With respect to subcutaneous injections, it is customary, in many cases, to pucker the flesh prior to applying the injection. Puckering the flesh has two main purposes. First, it isolates the portion of the body into which the injection is intended to be made and prevents the injection from inadvertently being made into underlying organs such as the muscles and the like where it might enter a large blood vessel prematurely. Puckering the flesh at the surface of the body essentially isolates the skin and its associated underlying structures including a subcutaneous adipose tissue or fat layer at the surface of the body. Puckering of the flesh also, in effect, hardens or firms that portion of the surface fascia facilitating insertion of the injection needle.

A medical professional such as a doctor or nurse will usually pucker the flesh with the fingers of one hand while applying the injection with the other hand. However, many injections, and insulin injections in particular, are applied by the patient him or herself since the frequency of the required injections mitigates against having a third party administer such injections. To have a medical person provide such injections would be prohibitively expensive unless such medical person was a member of the patient's family. While other members of a patient's family may also be able to apply insulin injections, this also is frequently inconvenient since an experienced hypodermic user in the patient's own family is not always present when the patient's medical injections are required. Consequently, it is customary for diabetes patients, if physically capable, to learn to administer their own injections of insulin. The same is true of patients requiring a few other medicinal substances that are provided by injection.

While it is possible for a patient to use two hands (assuming such patient has two operable hands) to inject medicinal substances into his own body such as into his thighs or abdominal area, it is physically impossible for a patient, using the flesh puckering technique, to make injections into his arms. This is because it is quite impossible for the normal person to reach a large portion of his arm with the hand of the same arm. Consequently, a number of devices have been developed for puckering the flesh prior to making an injection into such puckered flesh portion. Among such devices may be listed the following:

U.S. Pat. No. 1,934,046 issued Nov. 7, 1933 to M. DeMarchi discloses a vacuum-type apparatus arrangement for drawing the flesh of the body toward a hypodermic needle.

U.S. Pat. No. 2,660,169 issued Nov. 24, 1953 to H. Malm discloses a hypodermic syringe which includes two forceps or tweezer-like arms which may be used to gather or pucker flesh that may then be injected by a hypodermic needle positioned between the ends of the tweezer-like arms. Such arms have blunt ends which directly contact the flesh.

U.S. Pat. No. 2,704,071 issued Mar. 15, 1955 to P. Becker discloses a skin retractor for giving subcutaneous injections of adrenalin, insulin or formula B-12 for the treatment of pernicious anemia and the like. The device is said to be designed especially for subcutaneous injections rather than intravenous injections. The Becker device is essentially a conventional spring-clip having more or less U-shaped jaws with plastic surfaces. The top of the clip is provided with a lariat-type arrangement for holding with the hand to actively pull the clip and clamped skin between the jaws of the clip away from the body to facilitate injection.

U.S. Pat. No. 3,760,803 issued Sep. 25, 1973 to L. S. Boothby discloses a clamp designed to be applied to a body member such as an arm for self-injection of insulin or the like. The clip completely surrounds the arm and is provided with two transversely elongated jaws which may have compressible pads upon the surfaces. The spring-clip tends to compress a mound of flesh between the jaws to facilitate injection of a medicinal material into such flesh. It appears the Boothby self-injection clamp would not be particularly convenient to apply since the arm must first be inserted through the opening in the clamp.

U.S. Pat. No. 4,195,636 issued Apr. 1, 1980 to R. C. Behnke discloses a cross spring type clip for use particularly about the arm for puckering the flesh but also shown used for puckering relatively loose skin on the abdomen or the like preparatory to subcutaneous injection.

U.S. Pat. No. 4,223,673 issued Sep. 23, 1980 to W. J. Harris discloses a flesh-puckering clamp used for injection of subcutaneous substances. The clamp is provided with a pair of handles for expanding the jaws for application to the body. The jaws completely surround the arm and pucker the flesh on the opposite side of the arm from the handles.

U.S. Pat. No. 4,634,429 issued Jan. 6, 1987 to G. L. Schoettley discloses an arm encircling clamp arrangement for expediting self-injection of insulin and the like. The Schoettley clamp differs from the Boothby and Harris clamps in that the two jaws of Schoettley's clamp are not duplicates of each other, but are different. The one jaw is said to provide a broad surface against or upon which the opposing jaw tends to roll the flesh of the body providing a better support of said flesh for injection purposes.

Other devices which draw the flesh into a mound or pucker by vacuum means in order to facilitate insertion of a hypodermic needle are disclosed in U.S. Pat. No. 2,743,723, issued May 1, 1956 to G. N. Hein and U.S. Pat. No. 2,945,496 issued Jul. 19, 1960 to A. Fosdal, the latter being designed especially for use in dentistry.

Among prior patents that have been designed especially for facilitating intravenous injections may be mentioned the following:

U.S. Pat. No. 1,561,116 to J. C. Silliman (1925)
U.S. Pat. No. 2,103,174 to V. M. Posada (1937)
U.S. Pat. No. 3,324,854 to W. W. Weese (1967)
U.S. Pat. No. 4,299,219 to G. P. Norris (1981)
U.S. Pat. No. 4,314,568 to J. A. Loving (1982)
U.S. Pat. No. 4,586,924 to C. T. Lanning (1986)

The Norris device is a vacuum-type device, while the others are body surface pressure-type devices designed to accentuate a vein at the surface by single point constriction and lateral isolation.

French Patent 757,501 issued to M. G. Wilkinson in 1933 also discloses a skin puckering device rather similar to the Malma device noted above except that the injection needle is inserted into the puckered flesh from the side rather than from the top.

While the prior art devices for providing subcutaneous injections, particularly by the patient himself, have been effective within their limitations, they have been by and large complicated, expensive, difficult to use, or not as effective as desired.

In the applicants prior application there was also disclosed a special sharpened lip spring clip type prick device for puckering the skin prior to or to facilitate subcutaneous injection. The Applicant has now discovered that the efficiency and effectiveness of the prior described invention may be increased in accordance with the description and explanation particularly in conjunction with the arrangements shown in FIG. 23 through 28 described hereinafter.

OBJECTS OF THE INVENTION

It is, therefore, an object of the invention to provide a simple skin puckering or gathering device that will enable a patient to provide his own injections, particularly of insulin and the like, simply and effectively.

It is a further object of the invention to provide a skin puckering or gathering device that will allow the patient to provide his own injection using only one hand.

It is a still further object of the invention to provide a device of simple construction based on the spring-clip principle that allows a patient to conveniently and easily provide his own subcutaneous injections in any suitable or desired surface portion of the body that can be reached by one hand.

It is a still further object of the invention to provide a skin puckering or mounding device based upon a spring-clip construction which is simple and inexpensive to fabricate to an extent such that the devices can be dispensed by physicians to their patients as a service without charge.

It is a still further object of the invention to provide a skin puckering or mounding device of the spring clip-type in which the jaws of the device are provided with a particular construction which allows the device to easily grasp the flesh of the human body.

It is a still further object of the invention to provide a skin puckering or mounding device which is small and convenient and can be easily carried by the patient where ever he or she may be.

It is still further object of the invention to provide a skin puckering device of the spring-clip type which may be folded into a convenient small package which may be kept in a patient's pocket.

It is a still further object of the invention to provide an adjustable version of the invention that can be adjusted for use by relatively thinner and more obese patients.

BRIEF DESCRIPTION OF THE INVENTION

The present invention comprises a skin puckering or mounding device for use by a patient to pucker his own skin in various desirable portions of the body preparatory to the application of an injection of insulin, adrenalin or other medicament subcutaneously. The device of the invention is constructed of two separate arm portions pivoted or hinged together at a mid-point such that the arm portions on one side of the pivot comprise jaw portions for contact with the surface of the body while the arm portions on the opposite side of the pivot comprise handle portions arranged for convenient manual operation or control of the jaw portions. The handle portions may be formed or constructed from any convenient material, such as metallics, plastics, natural substances such as wood and the like. The jaw portion, on the other hand, must be made from a substance which, when shaped in the particular form of the jaws of the invention, will not tend to slip from the surface of the human body. Acceptable substances are, in general, any of the carbon based substances, natural or artificial, which have the surface characteristics essentially of wood. Such substances may comprise wood itself or wood products as well as some of the plastic materials having such surface characteristics. A spring arrangement is included in the puckering device to normally hold the jaws of the device closed with a force predetermined to be sufficient to pucker the skin of the normal human body.

The especially designed jaws of the device of the invention are in the form of a sharp edged configuration. These sharp edges or lips are opposed and are backed up by a fairly substantial portion of the jaw structure so that they are strong and durable. The sharp edges or lips of the jaw sections may have a substantially flat configuration or may, in some cases, be curved, but in any event, must be exactly opposing. It has been found that if the jaws of the clip are not in the shape described, they will not effectively grip the surface of the body, but will instead, slowly slip from such surface, making it impossible to use them for effectively puckering the skin for the application of injections to the body. The arm portions may be effectively either crossed or generally parallel in their operational configuration. A spring biasing device is arranged or incorporated to contact both arms and urge the jaws toward each other with the sharp edge lip configurations exactly opposite or opposing each other. There are a number of possible embodiments of the lip portion of the invention including multiple lips, undulating lips, lips formed from a suitable flesh contacting material different from the remainder of the material of the flesh puckering jaws and the like.

Several adjustable versions of the device of the invention are also shown and described.

BRIEF DESCRIPTION OF THE DRAWINGS

FIG. 1 shows an isometric view of a preferred flesh puckering clip in accordance with the invention held in a slightly open position.

FIG. 2 is a side view of the flesh puckering clip shown in FIG. 1 with the bottom outside jaw broken away to reveal the face of the opposed jaw.

FIG. 3 is a side view of the clip shown in FIGS. 1 and 2 showing the outline of the jaw section and particularly the sharp opposed portion of the jaws.

FIG. 4 is an isometric view of the preferred clip of the invention applied to the surface of the body, in the case illustrated an arm, to pucker the flesh of such arm preparatory to providing an injection into such flesh.

FIG. 5 shows an alternative embodiment of the skin puckering clip of the invention in which the extended skin contacting lips are positioned slightly in or displaced from the end of the clip.

FIG. 6 is an enlarged view of one of the clamp faces of the clip of FIG. 5 showing the flesh contacting lip.

FIG. 7 shows an alternative embodiment of the invention in which the handle portions of the arms of the clip may be folded to make the clip smaller for convenient storage or carrying in a patient's pocket or the like.

FIG. 8 shows a side view of the embodiment of FIG. 7 with the handles folded.

FIG. 8A is an enlargement of the detent used on the folding handles of the embodiment shown in FIGS. 7 and 8.

FIGS. 9, 10 and 11 show clamp face views of various alternative embodiments of the faces of the basic sharp lip jaw portions of the clip of the invention.

FIG. 12 shows a side view of the jaws of the embodiment of the invention shown in FIG. 11.

FIG. 23 is a side view of a further improved embodiment of the skin puckering device of the invention.

FIG. 24 is a side view of a still further improved embodiment of the device of the invention.

FIG. 25 is a side view of a still further improved embodiment of the invention showing an arrangement for adjustment of the pivot point.

FIG. 26 is a still further side view of an alternative arrangement for an adjustable device in accordance with the invention.

FIG. 27 is a side view of a still further alternative adjustable arrangement of a device in accordance with the invention.

FIG. 28 is an inside face view of a still further alternative embodiment of the invention.

DESCRIPTION OF THE PREFERRED EMBODIMENTS

Figure 13:
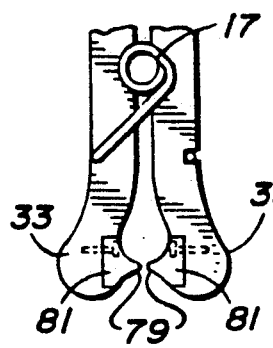
FIG. 13 shows the jaws of an embodiment of the invention wherein the opposed flesh puckering lips are made from a different material from the remainder of the jaws.

The present invention is an improved body puckering spring clip for convenient single or mono-handed application upon the body to allow the self-administration of medicinals to the body. Such medicinals may comprise insulin, adrenalin and the like which the patient may, through necessity, be required to self-administer. The device is made essentially in the form of a spring clip with a special jaw arrangement, such jaw being particularly adapted to effectively grasp the flesh at the surface of the body without slipping and hold such flesh firmly while an injection is made into such flesh, preferably between the jaws of the spring clip. The device is simple and inexpensive to manufacture, and because of this, is particularly adapted for widespread use by a variety of patients with different physical capacities. The construction, in fact, is so inexpensive that medical personnel are able to dispense the device to their patients as a service without charge so that such patients may be in a position to effectively and regularly administer their own medication.

The invention will be better understood by reference to the following description in the appended drawings in which:

FIG. 1 shows an isometric view of a preferred embodiment of the clip of the invention in which the clip 11 is comprised of two (2) pivoted arms 13 and 15 which are pivotally secured together as shown in a central location across a coiled spring wire pivot 17 which effectively connects the two arms 13 and 15 through spring clip extensions 19 and 21 extended to the outer surface of each of the arms. The upper portions 23 and 25 of the two arms 13 and 15 are preferably formed into handles 27 and 29 adapted for contact with the digits or fingers of one hand. The handles 27 and 29 are shaped as known in the art, for effective contact with the ends of the fingers. At the lower end of the arms 13 and 15 are located jaw members 33 and 35. Tee jaws 33 and 35 are laterally extended so that the jaw sections appear somewhat like abbreviated paddles. The additional width of the jaws provides additional contact with the skin and improves the interaction between the jaws of the device and the surface tissue of the patient. A fairly sharp or pointed portion of the face of each jaw 33 and 35 provides a protruding lip 37 and 39 on each jaw which actually contacts the surface tissue and gathers it together to form a mound or pucker in the skin and immediately underlying tissue into which an injection can be conveniently made with a hypodermic.

It will be understood, that when using the puckering device of the invention, the handles 27 and 29 will be usually manipulated between the thumb and the forefinger of the user to open the clip device by applying pressure to the upper portions 23 and 25 of the arms 13 and 15. The jaws 33 and 35 are then applied to the portion of the body into which it is wished to make the injection. After the device is pressed against the body, the pressure of the thumb and forefinger is relieved from the device so the spring clip extensions 19 and 21 can forcefully bias the two jaw members 33 and 35 towards each other. The coiled wire spring 17 and spring clip extensions 19 and 21 may be referred to broadly or as a unit as spring means 31. It will be understood, that prior to the jaw members being biased towards each other by the spring means 31, that the spring clip device must have been forcefully applied to the surface of the body at the point at which it is wished to pucker the skin for application of an injection to the body. When the force applied by the thumb and the forefinger of the user then is relieved from the handle portions 27 and 29, the jaws 33 and 35 of the spring clip device of the invention are forcefully biased toward each other by the spring means 31 so that the sharp or pointed portions 37 and 39 of the jaw forcefully contact the flesh of the surface of the body and as the jaw members are drawn towards each other, gather such flesh between the ends of the spring clip device into a mound or pucker into which an injection needle can then be conveniently passed. It will be understood that while the portions 37 and 39 are referred to as "sharp", such sharpness is relative and should not be so great as to actually cut or lacerate the surface of the body. Obviously, a surface which is too sharp will tend to cut into rather than gathering together or mounding the external flesh of the body.

It will be noted from FIGS. 1, 2 and 3, and particularly from FIG. 3, that the jaw portions of the spring clip have a particular shape including sharply defined leading jaw sections or lips 37 and 39 which, when the jaws are together, perfectly match. The jaw sections or lips 37 and 39 upon the two jaws 33 and 35 are shaped such that the sharpened outer end portion is very effectively backed up by solid backing portions 41 and 43 so that the sharpened or protruded lip portions are strong and durable. The spring clip-type puckering tool of the invention is shown in FIG. 4, attached or clamped onto a portion of the human body, i.e. in this case to the surface of an arm, preparatory to using a hypodermic needle for injecting a medicinal product such as insulin into the arm. The effectiveness of the puckering action can be easily seen in FIG. 4 and it will be understood that the insulin or other medication in the hypodermic 45 may be easily injected into such puckered flesh 47.

FIG. 5 shows a side view of an alternative embodiment of the invention in which the two arms 13 and 15, instead of being substantially parallel are instead visibly arcuate in outline and provided with molded jaw portions 49 and 51 with extended lips 52 and 54. The spring means 31 made up of the coil spring 17 and spring extensions 19 and 21 act in the same manner to force or urge the jaw sections 33 and 35 toward each other, thus closing the jaws 49 and 51 and puckering or mounding the skin and adjacent tissues constricted or caught between the lips 52 and 54. The arms of the jaw sections themselves, in FIG. 5, are the same as in FIGS. 1, 2 and 3 except that the angle and position of the lips 52 and 54 on the molded jaw portions 49 and 51 is somewhat changed so that the lips may be forced directly toward each other by the action of the spring means 31.

FIG. 6 shows a face view of one of the jaws of the spring clip shown in FIG. 5 illustrating the narrow elongated lip configuration centrally positioned upon the jaw portion 51.

FIG. 7 shows an improved embodiment of the invention in which upper pivot arm portions 23a and 25a are pivoted on pivot or hinge pins 53 and 55, which pass through pivot or hinge mountings 57 and 59 on both handle portions. The jaw portions of the clip shown in FIG. 7 are similar to those of FIG. 5, but, it will be understood, could be otherwise.

FIG. 8 shows the device of the invention illustrated in FIG. 7 with the pivot arm portions 23a and 25a folded into a compact position so that the device takes up less room and can be easily carried in the pocket of the user. It will be noted that the pivot arm portions have matching contact surfaces 61 which, when the pivot arms or handles are open, abut with a matching contact surface 63 on the main arm portions of the arms 13 and 14 so that pivot arms 23a and 25a, when they are being used, are biased by hand or finger pressure into open position. Any type of spring clip or other locking device may be also provided to effectively lock the handle portions into position for use. Such locking device needs to be easily unlocked to allow the handles to be folded into position for storage and the like. Consequently, it is very convenient to have the locking means comprised of two locking or securing devices 65 and 67 as shown in FIGS. 7 and 8. As shown, more particularly in FIG. 8A, these may comprise members mounted 65 mounted on the main body portions of the arms 13 and 14. A sliding arm 67 is mounted in a bracket 68 so it may slide up and down. A pin means 70 at the end of the sliding arm opposite the pivot or hinge points 53 or 55 may enter an opening in the folding handle portions 23a and 25a of the clip to maintain it in open position. In FIG. 7, the pivoted arm 67 of the securing means 65 is shown with the pin 70 engaged in locking position. As shown in FIG. 8A, a handle 71 may extend to the side to enable the pin 70 to be easily removed from the opening 70A in the folding sections 23a and 25a.

FIG. 9 is a view of the surface of one jaw of an alternative embodiment of the invention in which the lips of the jaw pieces are slightly corrugated or undulating as shown at 69 to improve the interaction with the flesh at the surface of the body. The lips are still maintained fairly sharp or pointed. The corrugations or undulations 69 preferably occur on matching opposed surfaces of the jaws where the flesh folds over when the device is in use and provides additional gripping with such folded over flesh.

FIG. 10 is a view of the surface of one jaw of an alternative embodiment of the invention in which the active jaw surface along the active skin contacting surface is dimpled for additional gripping. The dimples or small projections 74 extend from the surface of the lip 73 to provide additional skin contact and gripping, providing, in effect, more mechanical adhesion with the skin.

FIG. 11 also shows the face of one jaw of a still further alternative embodiment of the invention in which the jaws themselves are serrated to improve gripping with the surface of the human body. Normally such serration is not necessary. However, it can be more effective where the patient is, or tends to be, more oily-skinned than normal. The serrated portion 75 has some disadvantage in that it may have more tendency to irritate the skin.

FIG. 12 shows a side view of the multiply serrated jaws of a clip of the invention as shown in FIG. 11. The serrations constitute essentially multiple sharp lips. In FIG. 12 such lips are shown all the same height, but one might also advantageously extend beyond the others toward a matching lip on the other jaw.

Figure 14:
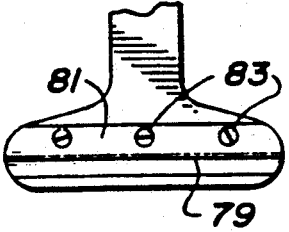
FIG. 14 is a face view of one of the jaws shown in FIG. 13 showing how the lip portions are attached to the jaw portions.

FIG. 13 is a side view of an embodiment of the invention in which the lip portion of the jaw of the puckering tool is formed from a separate piece or section. The lip 79 is, as shown in FIG. 13, mounted upon or integrally formed with a plate 81 which in the particular embodiment shown, comprises an inset or insert into the jaw portions 33 and 35 of the tool. As shown, the plate 81 may be demountably attached to the jaw sections by screw fastenings 83. The screw fastenings are best shown in FIG. 14 which is a view of the face of one of the jaws.

Figure 15:
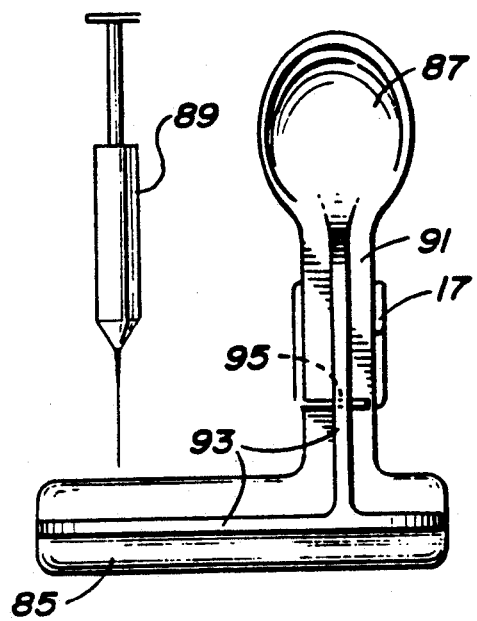
FIG. 15 is a lengthwise view of one jaw of a modified clip in accordance with the invention having an extension of the jaw on one side to facilitate injection between the jaws.

FIG. 15 shows a still further embodiment of the invention in which the jaw portions 85 of the invention are offset from the handle portions 87 so that the puckering of the skin occurs to the side of the device where it may be easily reached by an injection needle, such as a hypodermic or the like. In other words, the jaw 85 extends from one side of the device so that a hypodermic shown diagrammatically at 89 can be easily inserted between the jaws into the mounded or puckered skin between the jaws without interference from the handle portion 87. In FIG. 15 it will be seen that the jaws 85 are provided on the ends of support members 91, which are attached to the lower portions of the pivoted handle means 87. The arrangement allows, as indicated, the skin to be puckered away from the handle means, giving better access to the puckered portion during the injection.

Figure 16:
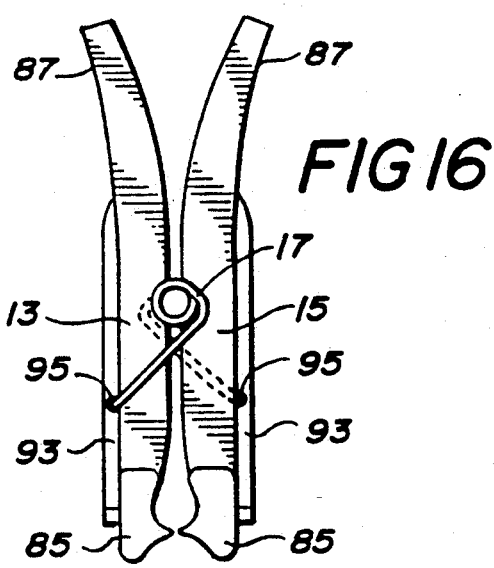
FIG. 16 is a view from the side of the clip of FIG. 15 showing reinforcing ridges on the back of the arms and jaws of the clip to prevent twisting of the device during use on the human body.

FIG. 16, shows a side view of the embodiment of the invention shown in FIG. 15 in which the pivoted arms of the skin puckering or mounding device are provided at the rear with an outwardly extending rib 93 that serves to reinforce the pivoted arms against bending or flexing which might interfere with gaining a secure grip upon the flesh of the body. Any vibration of the arms, or actually of the jaws of the device, during use or application to the body, tends to cause slippage of the jaws upon the surface of the body. The strengthening provided by the ribs 93 provides a sturdier construction without the bulk that might otherwise be required. The same spring biasing arrangement is used as in previous embodiments except that the spring clip extensions 19 and 21 extend through orifices 95 in the ribs 93 so that the extension bears directly against the back of the pivot arms 13 and 15.

Figure 17:
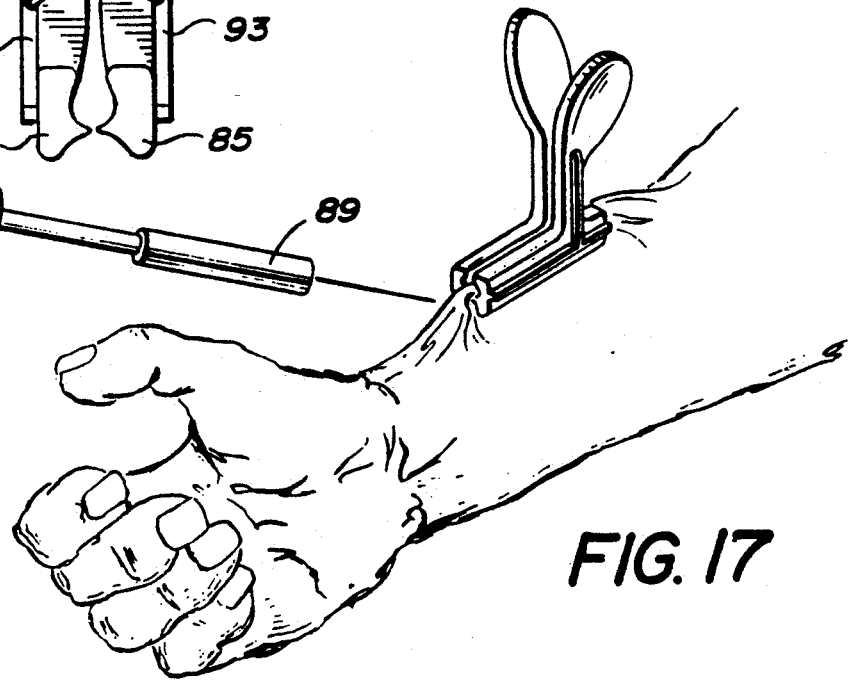
FIG. 17 is an isometric view of the clip of FIGS. 15 and 16 with the jaw applied to the flesh of a human arm.

FIG. 17 is an isometric view of the embodiment of the device shown in FIG. 16 applied to the surface of the body, in this case a section of an arm. It will be recognized that the ribs or webs 93 used as reinforcement in the embodiments of FIGS. 15 through 17 could be used also in other embodiments of the invention. It is particularly applicable to the embodiment of FIGS. 15-17, however, because of the offset position of the clamping jaws.

Figure 18:
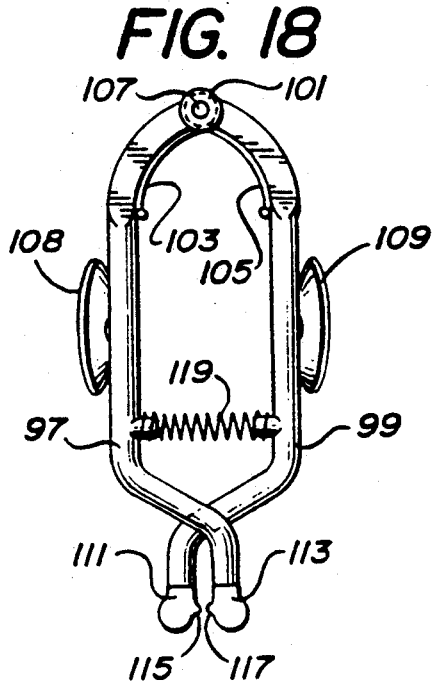
FIG. 18 shows an alternative embodiment of the invention in which the arms are pivoted together at the top and cross in the center to attach to opposite jaws.
Figure 19:
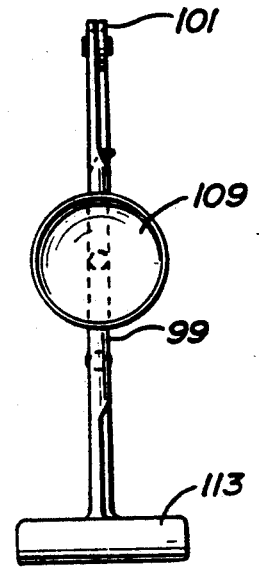
FIG. 19 is a side view of the embodiment of FIG. 18.

FIG. 18 shows a side view of an embodiment of the invention in which two pivot arms 97 and 99 of a clip in accordance with the invention are biased inwardly by spring pressure or force provided by a spring clip 101 having spring extensions 103 and 105. The spring clip coil 101 is centered about the pivot point 107 of the two arms 97 and 99 which are pivoted in this embodiment at the top of the arms rather than in the center. As may be seen in FIG. 19, the spring clip extensions 103 and 105 may extend down both sides of the pivoted arms. Two finger grips 108 and 109 may be provided upon the two arms of the device for applying force to open jaws 111 and 113 from which the skin contacting lips 115 and 117 extend. As may be seen in FIG. 19, which is a side view of the construction shown in FIG. 18, the two arms 97 and 99 are offset at the bottom so that they can extend by each other to enable biasing of the arms toward each other near the top by the spring means or to enable biasing of the arms 97 and 99 away from each other together with the jaw members 111 and 113 near the bottom by pressure on the finger grips 108 and 109. An auxiliary compression-type spring 119 may be provided between the arms 97 and 99 to aid in biasing such arms outwardly to bring the jaws 111 and 113 with the lips 115 and 117 together. Alternatively, the compression spring means 119 may completely replace the spring clip 101 or may be used in conjunction therewith as shown.

Figure 20:
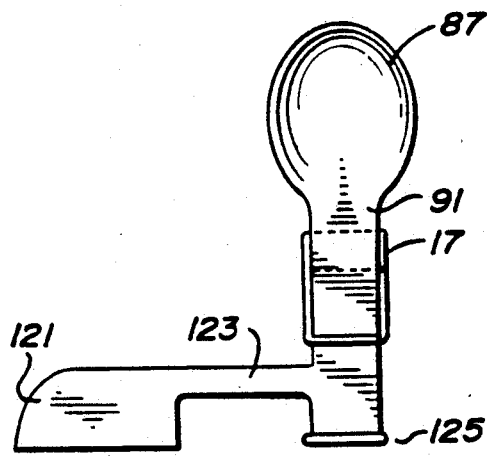
FIG. 20 shows an alternative embodiment of the invention in which the tissue puckering jaws are completely displaced laterally from the main or handle portion of the device.
Figure 21:
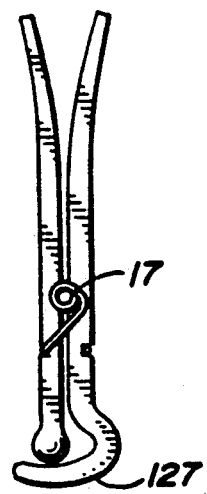
FIG. 21 is a side view of one embodiment of the arrangement shown in FIG. 20 including a rocker section on the main or handle portion of the device.
Figure 22:
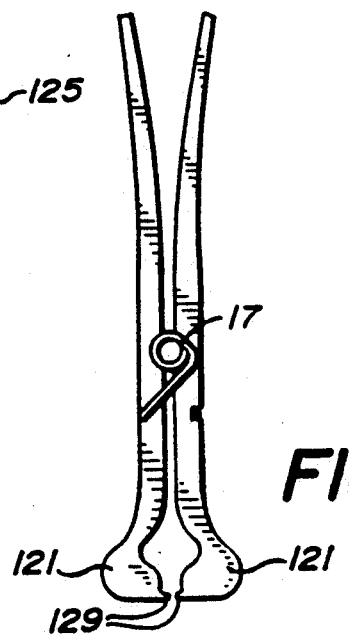
FIG. 22 is a side view of the embodiment of the invention shown in FIGS. 20 and 21 viewed from the opposite, or jaw side, of the clip.

FIG. 20 is a side view of a further embodiment of the invention somewhat similar to that shown in FIG. 15, but in which instead of the jaw members 85 merely extending to one side, the jaw member 121 is physically separated from the lower portion of the support member 91 by an extension member 123. The lower portion of the support member 91 or pivoted arm has a sliding support section 125 which contacts the surface of the body to steady the device as it is being operated to draw the flesh of the body into a pucker between the jaws 121, but such sliding support does not itself pucker the flesh, because it is not supplied with the protruding lips of the invention. In fact, it is preferable for the sliding support section to have a rounded lower and side contour so as to act as a rocker on the body surface. An arrangement such as this is shown in FIG. 21, which is an end view of the construction and shows one possible embodiment of a round rocker section 127 on one end of one of the support sections. An opposite end view of the same construction is shown in FIG. 22 and shows the two jaws 121 having the sharpened lips 129 of the invention contacting each other on the interior surfaces of the jaw members 121.

The present inventor has discovered that while the embodiments of his invention illustrated in FIGS. 1 through 22 are very effective, the efficiency and effectiveness can be increased by providing in effect wider possible adjustment in the opening between the sharp edges or lips of the jaws of the skin puckering device. This may be accomplished in several different manners and has been found to be particularly important when using the puckering tool of the invention on more obese persons where, because of the additional layer or layers of adipose tissue beneath or at the base of the skin, a wider jaw angle or opening may be necessary to gather between the lips of the puckering tool or device the same effective quantity of skin and subcutaneous adipose tissue or subcutaneous fat layer. The inventor has discovered, in other words, that the best results, and particularly the best grip upon the skin, is attained when a minimum amount of skin can be gathered within the jaws of the puckering device essentially so that the skin can be drawn upwardly into essentially a double layer with the outer layers of the skin or epidermis on the outside more or less facing away from each other and the underlying layers of the skin facing each other or against each other.

Since the subcutaneous adipose layer or layers tend to be drawn up with the skin and indeed the subcutaneous injection into the adipose tissue depends upon this, the more adipose tissue there is, the thicker the skin will in effect be and the farther away from each other the lips of the puckering device will be in operative position while holding the puckered skin ready to receive an injection. If insufficient tissue can be gathered between the lips, the puckered skin will assume a greater divergent angle between the jaws and the puckered skin is more likely to slip within the jaws. On the other hand, if too much relatively thin skin, i.e. without too much adipose tissue, the patient is likely to be more uncomfortable during the operation. Injection into the adipose tissue may also in such case be interfered with.

Consequently, it is not always satisfactory to merely arrange the jaws or lips of the puckering device of the invention to be capable of a wider opening, but it is advantageous to provide an adjustable arrangement so the jaws may be adjusted to suit the particular skin of the patient upon whom they are to be used. However, if the device is not to be made actually adjustable, then it will be advantageous if the device is to be used upon more obese persons for the pivot point of the jaws to be spaced either farther apart or otherwise adjusted to provide a wider spacing between the closed lips without changing the angle of the lips upon the skin.

FIG. 23 is a side view of an embodiment of the invention such as shown in FIG. 3 in which the same reference numerals are used to identify the same structures and parts, but in which a larger coiled wire spring designated 17a is used. This effectively moves the two jaw members 33 and 35 farther from each other in mid position as well as the two arms 13 and 15. This has been found to be significantly more effective with more corpulent individuals, while still effective with persons having less adipose tissue.

It should be pointed out at this point that while reference is had to persons with more adipose tissue or even more corpulent individuals, that reference is not had to really significantly overweight persons, but only to various degrees of subcutaneous adipose tissue within normal limits as well as, in some cases, abnormal limits. For example, the normal difference between the skins of men and women are included as well as the normal subcutaneous accumulation of more adipose tissue as a person ages up to a certain point, whereas if the person becomes quite elderly, such subcutaneous adipose tissue again begins to decrease. As indicated above, better, more comfortable results with the puckering device of the invention will be attained if such progressive changes can be followed and adjusted for by the puckering device of the invention.

Although preferable, it is not necessary for the two arms of the puckering device to be held farther apart from each other at all points by the pivoting mechanism. Instead, the pivot point or locations can be moved or repositioned to a location in which the arms upon which the clamp heads are mounted are enabled to be pivoted wider apart and then brought together. This may be seen in FIG. 24 in which an arrangement such as shown in FIG. 15 is shown and in which the same reference numerals designate similar structures. In FIG. 24 it will be seen that the spring clip 17 is the same as in FIG. 5, but has been moved to a higher location between the arms 13 and 15 where the curvature of the arms 13 and 15 has proceeded farther away from each other so that as the top of the arms are pressed towards each other the clamp heads 33 and 35 and their intersecting lips 52 and 54 are more rapidly and widely pulled apart. It will be noted that the size of the central coil 131 of the spring clip 17 is substantially the same size as shown in all the other Figures except FIG. 23 where the spring clip 17a is substantially larger to move the pivot point of the arm 13s and 15 apart.

FIG. 25 is a side view of a still further embodiment of the invention in which the basic structure is similar to that shown in FIGS. 1 and 23 and in which the same reference numerals designate the same structural features. It will be noted that in FIG. 25 the central coil of the spring clip 17 instead of being larger than in the other figures to, in effect, move the two arms 13 and 15 at their pivot points farther from each other, is instead the same size as in the other figures, except FIG. 23. The coil portion 131 of the spring clip 17 is, however, in FIG. 25 held or supported upon two wedge adjustments 133 which are longitudinally slideable in the grooves 135 provided on the backs of the arms 13 and 15. As may be seen in FIG. 25, when the wedge adjustments 133 are moved or slid downwardly in the grooves 135 the spring clip 17 is maintained in the same position longitudinally by reason of the ends or arms 19 of such spring clip 17 being retained in the grooves 21 on the backs of the arms 13 and 15 and consequently as the wedge adjustments 133 are slid downwardly in the grooves 135, the arms 13 and 15 are in effect wedged farther and farther apart providing additional distance between the jaw sections 33 and 35 which adapts the puckering device for use on more corpulent patients. If the top portions of the movable wedges 133 tend to contact each other at the top the two top portions of such wedges 133 may be reciprocally grooved or morticed so that the top portions may interdigitate and not interfere with movement of the arms 13 and 15 toward each other.

FIG. 26 shows in a side view similar to FIGS. 23 and 25 a variation of an adjustable pivot point in which the coil portion or coil 131 of the spring clip 17 is adjustable or movable longitudinally of the arms 13 and 15 moving the pivot point of the arms outwardly or inwardly as desired. Such adjustment is provided by a slide adjustment 137 which may be moved upwardly or downwardly. With each movement the arms of the spring clip are moved to appropriate grooves 21. As explained in connection with FIG. 24 when the pivot point is moved upwardly the balance or configuration of the device is changed so that the jaws 37 and 39 may be opened wider to accommodate additional adipose flesh under the skin as a whole.

FIG. 27 is a side view of an arrangement similar to that shown in FIG. 25 including an adjustment wedge means 133 provided to bias the pivot point in the form of a coil 131 of the spring clip 17 either outwardly or inwardly with respect to the arms 13 and 15. However, in FIG. 27, there are shown screw adjustment means 139 with outer handle means 141 to move the adjustment wedge means 133 either upwardly or downwardly within the grooves 135 in the back of the arms 13 and 15, it being understood that as the wedge adjustment means 133 are moved downwardly, the pivot point of both arms is in effect widened for use with more corpulent patients and when the wedge adjustment means 133 are moved upwardly, the pivot radius of the two arms 13 and 15 are moved closer to each other to accommodate less obese skin.

FIG. 28 is an inside view of one of the arms 13 or 15 showing a slide groove 135 in the handle defined by an upper edge 143, a lower edge 145 and two side bars or pieces 147, within which groove 135 the wedge adjustment means 133 may be seen positioned to slide either upwardly or downwardly as the result of rotation of a thumb wheel 149 mounted upon a bracket 151 and which has an outer toothed edge 153, or gear form for movable interengagement with a ratchet edge, not shown, on the side of the wedge adjustment means. Periodic grooves or seats 155 for the coil 131 of the spring clip means 17 are shown on the outside of the wedge adjustment means 133 in FIG. 28.

As will be seen from the description above, the invention provides a very convenient and effective means for puckering the skin prior to the administration of subcutaneous injections into the human body.

While the present invention has been described at some length and with some particularity with regard to several embodiments, it is not intended that the invention be limited to any such particulars or embodiments, but it is to be construed broadly with reference to the appended claims so as to provide the broadest possible interpretation of such claims in view of the prior art and thereby to effectively encompass the intended scope of the invention.

I claim:

1. A flesh puckering device for self-administration of injections of medicinal fluids comprising:
    (a) a pair of elongated lever arm means effectively pivoted to each other between the ends,
    (b) a pair of laterally extended opposed jaw means mounted upon one end of each of the pair of elongated lever arm means, said jaws having opposed faces,
    (c) handle means positioned upon a portion of said elongated lever arm means removed from the jaw means,
    (d) resilient means arranged and constructed to bias the elongated lever arm means to move the jaw means along with their opposed faces toward each other,
    (e) each jaw means having a sharply tapered elongated contour extending outwardly from the face of said jaw means in the direction of the other jaw means and directly opposed to the sharply tapered elongated contour of the other jaw means providing a narrow laterally extended intersecting pair of sharply tapered lips for application to the surface of a living human body and being biased toward each other by the resilient means, for gathering a portion of flesh between them and retaining it in position for insertion of a hollow needle thereinto,
    (f) means for adjusting and coordinating the position of the pivot point of the lever arm means as well as the distance apart of the lever arm means at said pivot point such as to allow the jaw means to encompass a double fold of skin and underlying adipose tissue easily between the elongated sharply tapered lips of the jaws while such elongated tapered lips are maintained substantially oriented toward each other.

2. A flesh puckering device in accordance with claim 1 wherein the distance between the elongated lever arm means is adjustable by providing different dimensioned pivoting means.

3. A flesh puckering device in accordance with claim 2 wherein the pivot means comprises the coil of a spring clip means.

4. A flesh puckering device in accordance with claim 1 wherein the distance between the elongated lever arm means is made adjustable by a mechanical adjustment means.

5. A flesh puckering device in accordance with claim 4 wherein the mechanical adjustment means comprises a sliding wedge-type adjustment means.

6. A flesh pushing device in accordance with claim 7 wherein the sliding wedge-type adjustment means is arranged to be moved by a rotating adjustment.

7. A flesh puckering device in accordance with claim 1 wherein the longitudinal position of the pivot point is adjustable to adapt said position to the amount of subcutaneous adipose tissue of the living human body.

8. A flesh puckering device in accordance with claim 7 wherein the position of the pivot point is adjustable by moving the pivot point to predetermined structurally retained locations.

9. A flesh puckering device in accordance with claim 7 wherein the longitudinal position of the pivot point is made adjustable by a mechanical adjustment means.

10. A flesh puckering device in accordance with claim 9 wherein the mechanical adjustment means comprises a sliding pivot seat-type adjustment means.

11. A flesh puckering device in accordance with claim 10 wherein the sliding pivot seat-type means is arranged and constructed to be movable by means of a rotating adjustment.

12. A method of self-administration of medicinal injections comprising:
    (a) adjusting the maximum opening between a pair of jaws of a skin puckering device by movably adjusting a pivot point of two pivoting elongated arms of said puckering device, having an overall shape allowing such adjustment to adapt the maximum opening via said pivot point adjustment to the relative obeseness of a living human body the possessor of which is to self-administer an injection, said elongated arms having a jaw at one end of each arm, said jaws having opposed laterally extended relatively sharp ridge sections, (b) applying two opposed laterally extended relatively sharp ridge sections to the surface of said living human body in a position somewhat spaced from each other in open position, (c) forcefully biasing the sharp ridge sections toward each other by continuous spring action to gather a portion of flesh between said relatively sharp ridge sections followed by holding said flesh in position between the sharp ridge sections, and (d) inserting a needle in said gathered flesh and injecting a medicinal substance through the needle.

13. A method of self-administration of medicinal injections in accordance with claim 12 wherein the longitudinal position of the pivot point is adjusted.

14. A method of self-administration of medicinal injections in accordance with claim 13 wherein the longitudinal position of the pivot point is adjucted by means of mechanical adjustment means incorporated into the elongated pivot arms.

15. A method of self-administration of medicinal injections comprising:

(a) manipulating an adjustment means for distantly seperating a pivot point and adjacently positioned two pivoting elongated arms of a skin puckering device to adapt said pivot point to the relative obeseness of a living human body the possessor of which is to self-administer an injection, said elongated arms having upon one end of each arm opposed laterally extended relatively sharp ridge sections, (b) applying two opposed laterally extended relatively sharp ridge sections to the surface of said living human body in a position somewhat spaced from each other in open position, (c) forcefully biasing the sharp ridge sections toward each other by continuos spring action to gather a portion of flesh between said relatively sharp ridge sections followed by holding said flesh in position between the sharp ridge sections, and (d) inserting a needle in said gathered flesh and injecting a medicinal substance through the needle.

16. A method of self-administration of medicianl injections in accordance with claim 15 wherein the distance between said arms and the pivot point is adjusted by mechanical adjustment means incorporated upon the elongated pivot arms.

* * * * *